US008884072B2

(12) United States Patent
Miller et al.

(10) Patent No.: US 8,884,072 B2
(45) Date of Patent: Nov. 11, 2014

(54) MITIGATION OF FOULING IN HYDROFORMYLATION PROCESSES BY WATER ADDITION

(75) Inventors: Glenn A. Miller, South Charleston, WV (US); Michael A. Brammer, Lake Jackson, TX (US); Donald L. Campbell, Jr., Sorrento, LA (US); Thomas C. Eisenschmid, Cross Lanes, WV (US); Adrian Lord, London (GB); Jens Rudolph, Worms (DE); Hans-Rüdiger Reeh, Einselthum (DE); Hans-Günter Thelen, Mannheim (DE); Maximilian Walter, Neustadt an der Weinstrasse (DE)

(73) Assignees: Dow Technology Investments LLC, Midland, MI (US); BASF SE, Ludwigshafen (DE)

( * ) Notice: Subject to any disclaimer, the term of this patent is extended or adjusted under 35 U.S.C. 154(b) by 0 days.

(21) Appl. No.: 13/885,033

(22) PCT Filed: Nov. 3, 2011

(86) PCT No.: PCT/US2011/059153
§ 371 (c)(1),
(2), (4) Date: Jun. 12, 2013

(87) PCT Pub. No.: WO2012/064586
PCT Pub. Date: May 18, 2012

(65) Prior Publication Data
US 2013/0261344 A1 Oct. 3, 2013

Related U.S. Application Data

(60) Provisional application No. 61/412,983, filed on Nov. 12, 2010.

(51) Int. Cl.
*C07C 45/50* (2006.01)
*C07C 45/80* (2006.01)

(52) U.S. Cl.
CPC .............. *C07C 45/505* (2013.01); *C07C 45/80* (2013.01)
USPC ........................................................ 568/454

(58) Field of Classification Search
USPC ........................................................ 568/454
See application file for complete search history.

(56) References Cited

U.S. PATENT DOCUMENTS

| | | |
|---|---|---|
| 3,527,809 A | 9/1970 | Pruett et al. |
| 4,148,830 A | 4/1979 | Pruett et al. |
| 4,247,486 A | 1/1981 | Brewester et al. |
| 4,518,809 A | 5/1985 | Forster et al. |
| 4,528,403 A | 7/1985 | Tano et al. |
| 4,593,127 A | 6/1986 | Bunning et al. |
| 4,668,651 A | 5/1987 | Billig et al. |
| 4,717,775 A | 1/1988 | Billig et al. |
| 4,769,498 A | 9/1988 | Billig et al. |
| 4,774,361 A | 9/1988 | Maher et al. |
| 4,861,918 A | 8/1989 | Miller et al. |
| 4,885,401 A | 12/1989 | Billig et al. |
| 5,102,505 A | 4/1992 | Sorensen |
| 5,110,990 A | 5/1992 | Blessing et al. |
| 5,264,616 A | 11/1993 | Roeper et al. |
| 5,288,918 A | 2/1994 | Maher et al. |
| 5,312,996 A | 5/1994 | Packett |
| 5,360,938 A | 11/1994 | Babin et al. |
| 5,364,950 A | 11/1994 | Babin et al. |
| 5,430,194 A | 7/1995 | Barner et al. |
| 5,491,266 A | 2/1996 | Babin et al. |
| 5,710,344 A | 1/1998 | Breikss et al. |
| 5,741,944 A | 4/1998 | Bryant et al. |
| 5,741,945 A | 4/1998 | Bryant et al. |
| 5,744,649 A | 4/1998 | Bryant et al. |
| 5,886,235 A | 3/1999 | Bryant et al. |
| 5,892,119 A | 4/1999 | Bryant et al. |
| 5,917,095 A | 6/1999 | Bryant et al. |
| 5,932,772 A | 8/1999 | Argyropoulos et al. |
| 5,952,530 A | 9/1999 | Argyropoulos et al. |
| 6,265,620 B1 | 7/2001 | Urata et al. |
| 6,440,891 B1 | 8/2002 | Maas et al. |
| 7,009,068 B2 | 3/2006 | Schmutzler et al. |
| 7,145,042 B2 | 12/2006 | Volland et al. |
| 7,196,230 B2 | 3/2007 | Peng et al. |
| 7,586,010 B2 | 9/2009 | Liu et al. |
| 2009/0171121 A1 | 7/2009 | Liu et al. |
| 2009/0299099 A1 | 12/2009 | Tolleson et al. |

FOREIGN PATENT DOCUMENTS

| | | |
|---|---|---|
| EP | 0357997 A1 | 3/1990 |
| WO | 88/08835 A1 | 11/1988 |
| WO | 97/20794 A1 | 6/1997 |
| WO | 2005/042458 A2 | 5/2005 |
| WO | 2008/071508 A1 | 6/2008 |

*Primary Examiner* — Sikarl Witherspoon
(74) *Attorney, Agent, or Firm* — Whyte Hirschboeck Dudek S.C.

(57) ABSTRACT

The extraction process for removing metal salts from an organic hydroformylation reaction fluid ("HRF") prior to returning the HRF to a reaction zone of a hydroformylation process, the extraction process comprising the step of contacting the HRF with an aqueous buffer solution, is improved by contacting the HRF with water in addition to that present in the aqueous buffer solution, i.e., with added water.

14 Claims, 3 Drawing Sheets

MITIGATION OF FOULING IN HYDROFORMYLATION PROCESSES BY WATER ADDITION

CROSS REFERENCE TO RELATED APPLICATION

The present application is the national phase of PCT Patent Application No. PCT/US2011/059153 filed Nov. 3, 2011, which claims priority to U.S. Provisional Application No. 61/412,983, filed Nov. 12, 2010, the entire content of which is incorporated by reference herein.

BACKGROUND OF THE INVENTION

1. Field of the Invention

This invention relates to hydroformylation processes. In one aspect the invention relates to the mitigation of fouling in hydroformylation processes while in another aspect, the invention relates to the mitigation of fouling in such processes by the addition of water.

2. Description of the Related Art

In the rhodium/bisphosphite-catalyzed hydroformylation of olefins, the bisphosphite ligand slowly and inexorably degrades to a number of byproducts. Some of these byproducts are acidic, and may be removed by contacting the reaction solution with an aqueous buffer (e.g. sodium phosphate). The resulting metal salts are appreciably soluble in water, and can be effectively removed from the organic phase. This extraction process is described in WO 97/20794.

Following contact with the aqueous buffer, the organic phase is returned to the reactor system. Although the two phases are immiscible, some gradual entrainment of aqueous buffer into the reactor may occur. Upset conditions may also cause episodic, inadvertent carryover of aqueous buffer into the reaction process. The result is the formation of acid metal salts in the reaction system.

Although the acid metal salts are soluble in water, they are sparingly soluble in the organic matrix. Surprisingly they may also swell and/or become sticky when the water level of the organic matrix is 0.1 percent by weight or greater. This gelatinous, sticky material can cling to cool surfaces, e.g., heat exchangers, control valves, distributors, etc., and, in turn, reduce their operating efficiency.

SUMMARY OF THE INVENTION

In one embodiment the invention is an extraction process for removing metal salts from an organic hydroformylation reaction fluid ("HRF") prior to returning the HRF to a reaction zone of a hydroformylation process. The HRF comprises an organophosphorous ligand and a metal-organophosphorous ligand complex, and the extraction process comprises the step of contacting the HRF with an aqueous buffer solution within an extraction zone of the hydroformylation process. The reaction zone is located upstream of the extraction zone, and the extraction process is improved by contacting the HRF with water outside of the extraction zone in addition to that present in the aqueous buffer solution. The aqueous buffer solution is used to stabilize the organophosphorous ligand against hydrolytic degradation and the metal-organophosphorous ligand complex against degradation or deactivation and to remove or reduce the degradation products from the HRF.

In one embodiment the added water is contacted with the HRF prior to the extraction zone of the hydroformylation process, e.g., in the reaction zone or a separation zone, both located upstream of the extraction zone. In one embodiment the hydroformylation process further comprises heat exchangers, and the added water is contacted with the HRF upstream of the heat exchangers. In one embodiment the added water is not buffered, and in one embodiment the added water is buffered but at a concentration of no greater than ten percent of the aqueous buffer solution.

DETAILED DESCRIPTION OF THE PREFERRED EMBODIMENT

Definitions

Figure 1:
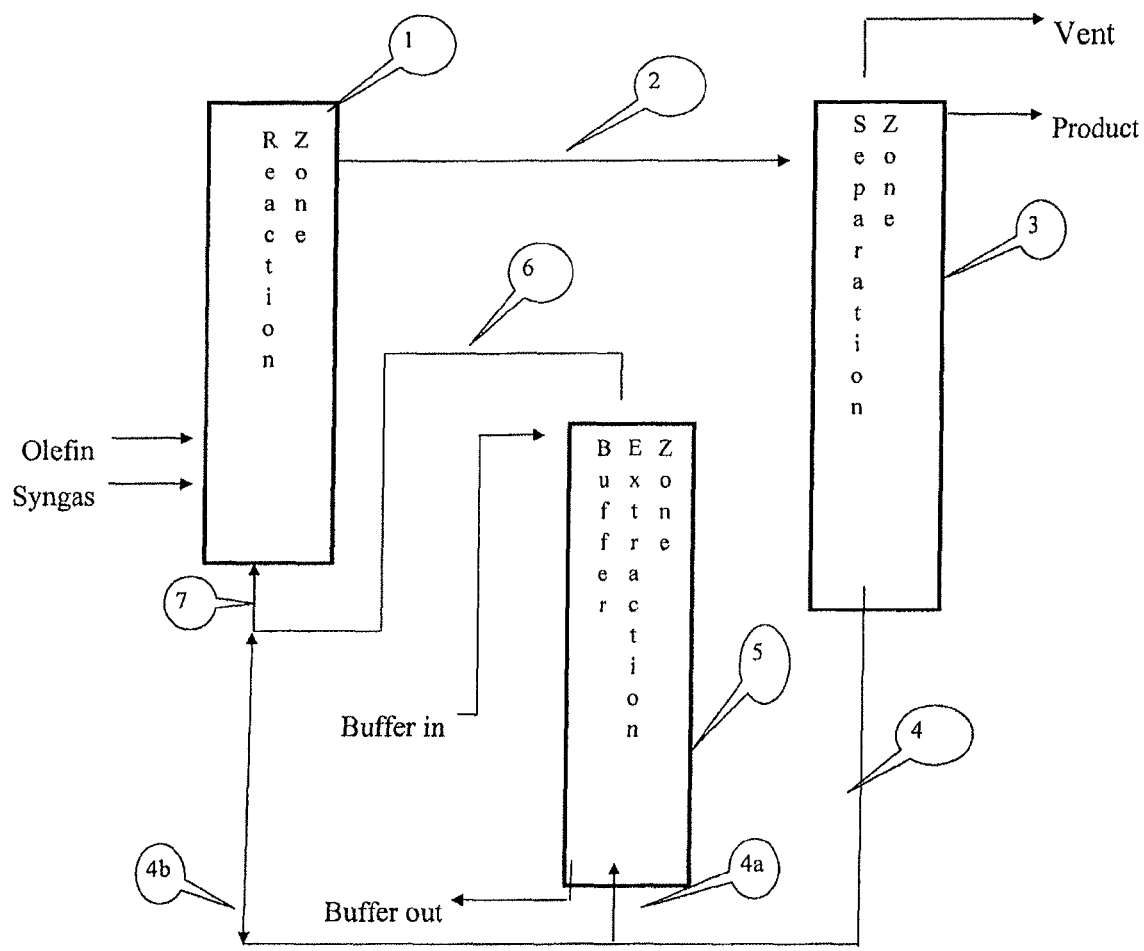
FIG. 1 is a schematic illustration of the process of the invention showing the positions of the reaction, buffer extraction and separation zones relative to one another, and various points in the process for water addition.

All references to the Periodic Table of the Elements and the various groups within the Table are to the Table as published in the CRC Handbook of Chemistry and Physics, $71^{st}$ Ed. (1990-1991), CRC Press, at page 1-10. Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, etc., is from 100 to 1,000, then all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the amount of water added to either the hydroformylation reaction mass and/or product.

"Hydroformylation" includes, but is not limited to, all permissible asymmetric and non-asymmetric hydroformylation processes which involve converting one or more substituted or unsubstituted olefinic compounds, or a reaction mixture comprising one or more substituted or unsubstituted olefinic compounds, to one or more substituted or unsubstituted aldehydes or a reaction mixture comprising one or more substituted or unsubstituted aldehydes.

"Hydroformylation reaction fluid" or "HRF" includes, but is not limited to, a reaction mixture containing an amount of any one or more of the following: (a) a metal-organophosphorous ligand complex catalyst, (b) free organophosphorous ligand, (c) one or more phosphorus acidic compounds formed in the reaction (which may be homogeneous or heterogeneous, and these compounds include those adhered to process equipment surfaces), (d) aldehyde product formed in the reaction, (e) unreacted reactants, and (f) an organic solubilizing agent for said metal-organophosphorous ligand complex catalyst and said free organophosphorous ligand in which the ligand is a hydrolysable phosphorous ligand. The reaction product fluid encompasses, but is not limited to, (a) the reaction medium in a reaction zone, (b) the reaction medium stream on its way to a separation zone, (c) the reaction medium in the separation zone, (d) the recycle stream between the separation zone and the reaction zone, (e) the reaction medium withdrawn from the reaction zone or separation zone for treatment with an aqueous buffer solution, (f) the withdrawn reaction medium treated with the aqueous buffer solution, (g) the treated reaction medium returned to the reaction zone or separation zone, (h) the reaction medium in an external cooler, and (i) ligand decomposition products or their salts formed in the HRF and precipitated or deposited on the surfaces of the process equipment.

"Hydrolysable phosphorous ligands" are ligands that contain at least one trivalent phosphorous atom and that has at least one P—X bond wherein X is oxygen, nitrogen, chloride, fluoride or bromide. Examples include but are not limited to phosphites, bisphosphites, phosphonites, bisphosphonites, phosphinites, phosphoramidites, bisphosphoramidites, fluorophosphites, chelate structures including different P—X moieties, and chelating structures of mixed structure such as phosphino-phosphites, phosphino-phosphoramidites and the like.

"Complex" means a coordination compound formed by the union of one or more electronically rich molecules or atoms capable of independent existence with one or more electronically poor molecules or atoms, each of which is also capable of independent existence.

"Upstream" means that a zone or step of a process is located or performed before that of a reference zone or step, e.g., the reaction zone of the hydroformylation process is located before or upstream of the separation zone which is located before or upstream of the extraction zone.

"Downstream" means that a zone or step of a process is located or performed after that of a reference zone or step, e.g., the extraction zone of the hydroformylation process is located after or downstream of the separation zone which is located after or downstream of the reaction zone.

Hydroformylation Process

The hydroformylation processes of this invention may be asymmetric or non-asymmetric, the preferred processes being non-asymmetric, and may be conducted in any continuous or semi-continuous fashion and may involve any catalyst liquid and/or gas recycle operation desired. Thus it should be clear that the particular hydroformylation process for producing such aldehydes from an olefinic unsaturated compound, as well as the reaction conditions and ingredients of the hydroformylation process are not critical features of this invention.

Illustrative metal-organophosphorous ligand complex catalyzed hydroformylation processes which may experience such hydrolytic degradation include those processes as described, for example, in U.S. Pat. Nos. 4,148,830; 4,593,127; 4,769,498; 4,717,775; 4,774,361; 4,885,401; 5,264,616; 5,288,918; 5,360,938; 5,364,950; 5,491,266 and 7,196,230. Likewise other P—X containing species that will likely under-go similar hydrolytic degradation include organophosphonites, phosphoramidites, fluorophosphonites, and the like such as described in U.S. Pat. No. 7,009,068, WO 2008/071508 U.S. Pat. No. 5,710,344, WO 2005/042458, U.S. Pat. No. 7,145,042, U.S. Pat. No. 6,440,891, U.S. Pat. No. 7,586,010, US Published Patent Applications 2009/0171121 and 2009/0299099, and U.S. Pat. No. 6,265,620. These species will generate a variety of acidic and/or polar degradation products that can be extracted by use of the extractor technology taught in U.S. Pat. Nos. 5,744,649 and 5,741,944. Accordingly, the hydroformylation processing techniques of this invention may correspond to any known processing techniques. Preferred processes are those involving catalyst liquid recycle hydroformylation processes.

In general, such catalyst liquid recycle hydroformylation processes involve the production of aldehydes by the reaction of an olefinic unsaturated compound with carbon monoxide and hydrogen in the presence of a metal-organophosphorous ligand complex catalyst in a liquid medium that also contains an organic solvent for the catalyst and ligand. Preferably free organophosphorous ligand is also present in the liquid hydroformylation reaction medium. By "free organophosphorous ligand" is meant organophosphorous ligand that is not complexed with (tied to or bound to) the metal, e.g., metal atom, of the complex catalyst. The recycle procedure generally involves withdrawing a portion of the liquid reaction medium containing the catalyst and aldehyde product from the hydroformylation reactor (i.e., reaction zone), either continuously or intermittently, and recovering the aldehyde product therefrom by use of a composite membrane such as disclosed in U.S. Pat. No. 5,430,194, phase separation as disclosed in U.S. Pat. Nos. 5,932,772 and 5,952,530, or by the more conventional and preferred method of distilling it (i.e., vaporization separation) in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and synthesis gas, can be recycled in any desired manner to the hydroformylation zone (reactor). The recovered metal catalyst containing residue of such membrane separation or recovered non-volatilized metal catalyst containing residue of such vaporization separation can be recycled, to the hydroformylation zone (reactor) in any conventional manner desired.

In a preferred embodiment the hydroformylation reaction product fluids include any fluid derived from any corresponding hydroformylation process that contains at least some amount of four different main ingredients or components, i.e., the aldehyde product, a metal-organophosphorous ligand complex catalyst, free organophosphorous ligand and an organic solubilizing agent for said catalyst and said free ligand, said ingredients corresponding to those employed and/or produced by the hydroformylation process from whence the hydroformylation reaction mixture starting material may be derived. The hydroformylation reaction mixture compositions employable herein can and normally will contain minor amounts of additional ingredients such as those which have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials and/or ligand degradation products and adducts thereof, and high boiling liquid aldehyde condensation byproducts, as well as other inert co-solvent type materials or hydrocarbon additives, if employed.

Illustrative metal-organophosphorous ligand complex catalysts employable in such hydroformylation reactions encompassed by this invention as well as methods for their preparation are well known in the art and include those disclosed in the above mentioned patents. In general such catalysts may be preformed or formed in situ as described in such references and consist essentially of metal in complex combination with an organophosphorous ligand. Carbon monoxide may also be present and complexed with the metal in the active species. The active species may also contain hydrogen directly bonded to the metal.

The catalyst useful in the hydroformylation process includes a metal-organophosphorous ligand complex catalyst which can be optically active or non-optically active. The permissible metals which make up the metal-organophosphorous ligand complexes include Group 7, 8, 9 and 10 metals selected from rhodium (Rh), cobalt (Co), iridium (Ir), ruthenium (Ru), iron (Fe), nickel (Ni), palladium (Pd), platinum (Pt), osmium (Os) and rhenium (Re) with the preferred metals being rhodium, cobalt, iridium and ruthenium, more preferably rhodium, cobalt and ruthenium, especially rhodium. Mixtures of metals from Groups 7, 8, 9 and 10 may also be used in this invention. The permissible organophosphite ligands which make up the metal-organophosphorous ligand complexes and free organophosphorous ligand include mono-, di-, tri- and higher polyorganophosphonites, polyorganophosphoramidites, polyorganophosphinites, polyorganophosphonites, polyorganofluorophosphites, and the like. Mixtures of such ligands may be employed if desired in the metal-organophosphorous ligand complex catalyst and/or free ligand and such mixtures may be the same or different. This invention is not limited in any manner by the permissible organophosphorous ligands or mixtures thereof. The successful practice of this invention does not depend and is not predicated on the exact structure of the metal-organophosphorous ligand complex species, which may be present in their mononuclear, binuclear and/or higher nuclearity forms. Indeed, the exact structure is not known. The catalytic species may, in its simplest form, consist essentially of the metal in complex combination with the organophosphorous ligand and carbon monoxide and/or hydrogen when used.

The organophosphorous ligands that may be employed in the practice of this invention may possess at least one P—X bond and one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and RP(O)(OH)O (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3$, $CH_2$=$CHCH_2$, $CH_3CH$=$CHCH_2$, $C_6H_5CN$, $CH_3CN$, $NH_3$, pyridine, $(C_2H_5)_3N$, mono-olefins, di-olefins and tri-olefins, tetrahydrofuran, and the like. The complex species are preferably free of any additional organic ligand or anion that might poison the catalyst or have an undue adverse effect on catalyst performance. In the metal-organophosphorous ligand complex catalyzed hydroformylation reactions, preferably the active catalysts are free of sulfur directly bonded to the metal, although such may not be absolutely necessary.

The number of available coordination sites on such metals is well known in the art. Thus the catalytic species may comprise a complex catalyst mixture, in their monomeric, dimeric or higher nuclearity forms, which are preferably characterized by at least one organophosphorous-containing molecule complexed per one molecule of metal, e.g., rhodium. For instance, the catalytic species of the preferred catalyst employed in a hydroformylation reaction may be complexed with carbon monoxide and hydrogen in addition to the organophosphorous ligands in view of the carbon monoxide and hydrogen gas employed by the hydroformylation reaction. The process of this invention can also employ hydroformylation complex catalysts having multi-metal centers.

The organo-phosphorous compounds that may serve as the ligand of the metal-organophosphorous ligand complex catalyst and/or free ligand of the hydroformylation processes and reaction product fluids of this invention may be of the achiral (optically inactive) or chiral (optically active) type and are well known in the art. Achiral organo-phosphites are preferred.

Among the organo-phosphorous compounds that may serve as the ligand of the metal-organophosphorous ligand complex catalyst of this invention and/or any free organo-phosphorous ligand of the hydroformylation process that might also be present in said reaction product fluids are mono-organophosphite, di-organophosphite, tri-organophosphite and organopolyphosphite compounds or combinations and mixtures thereof. Such organophosphite ligands employable in this invention and/or methods for their preparation are well known in the art, and representative ligands are described in, among other references, U.S. Pat. No. 5,741,944. Likewise other P—X containing species such as organophosphonites, phosphoramidites, fluorophosphonites, and the like are readily prepared as described in the patents cited above.

As noted above, the metal-organophosphorous ligand complex catalysts employable in this invention may be formed by methods known in the art. The metal-organophosphorous ligand complex catalysts may be in homogeneous or heterogeneous form. For instance, preformed rhodium hydrido-carbonyl-organophosphorous ligand catalysts may be prepared and introduced into the reaction mixture of a hydroformylation process. More preferably, the rhodium-organophosphorous ligand complex catalysts can be derived from a rhodium catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorous ligand for the in situ formation of the active catalyst. In a preferred embodiment of this invention, rhodium dicarbonyl acetylacetonate is employed as a rhodium precursor and reacted in the presence of a solvent with the organophosphorous ligand to form a catalytic rhodium-organophosphorous ligand complex precursor which is introduced into the reactor along with excess (free) organophosphorous ligand for the in situ formation of the active catalyst. In any event, for the purpose of this invention carbon monoxide, hydrogen and organophosphorous compound are all ligands that are capable of being complexed with the metal and that an active metal-organophosphorous ligand catalyst is present in the reaction mixture under the conditions used in the hydroformylation reaction.

In addition to the metal-organophosphorous ligand complex catalyst, free organophosphorous ligand (i.e., ligand that is not complexed with the metal) may also be present in the hydroformylation reaction medium. The free organophosphorous ligand may correspond to any of the above-defined organophosphorous ligands discussed above as employable herein. Preferably the free organophosphorous ligand is the same as the organophosphorous ligand of the metal-organophosphorous ligand complex catalyst employed. However, such ligands need not be the same in any given process. The hydroformylation process of this invention may involve from 0.1 moles or less to 100 moles or higher, of free organophosphorous ligand per mole of metal in the hydroformylation reaction medium. Preferably the hydroformylation process of this invention is carried out in the presence of from 1 to 50 moles of organophosphorous ligand, and more preferably for organopolyphosphorous from 1.1 to 4 moles of organopolyphosphorous ligand, per mole of metal present in the reaction medium; said amounts of organophosphorous ligand being the sum of both the amount of organophosphite ligand that is bound (complexed) to the metal present and the amount of free (non-complexed) organophosphorous ligand present. Since it is more preferred to produce non-optically active aldehydes by hydroformylating achiral olefins, the more preferred organophosphorous ligands are achiral type organophosphorous ligands. Of course, if desired, make-up or additional organophosphorous ligand can be supplied to the reaction medium of the hydroformylation process at any time and in any suitable manner, e.g. to maintain a predetermined level of free ligand in the reaction medium.

The hydroformylation catalyst may be in heterogeneous form during the reaction and/or during the product separation. Such catalysts are particularly advantageous in the hydroformylation of olefins to produce high boiling or thermally sensitive aldehydes, so that the catalyst may be separated from the products by filtration or decantation at low temperatures. For example, the rhodium catalyst may be attached to a support so that the catalyst retains its solid form during both the hydroformylation and separation stages, or is soluble in a liquid reaction medium at high temperatures and then is precipitated on cooling.

The substituted or unsubstituted olefinic unsaturated starting material reactants that may be employed in the hydroformylation processes of this invention include both optically active (prochiral and chiral) and non-optically active (achiral) olefinic unsaturated compounds containing from 2 to 40, preferably 3 to 20, carbon atoms. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403). Moreover, such olefin compounds may further contain one or more ethylenic unsaturated groups, and of course, mixtures of two or more different olefinic unsaturated compounds may be employed as the starting hydroformylation material if desired. For example, commercial alpha olefins containing four or more carbon atoms may contain minor amounts of corresponding internal olefins and/or their corresponding saturated hydrocarbon and such commercial olefins need not necessarily be purified from same prior to being hydroformylated. Illustrative mixtures of olefinic starting materials that can be employed in the hydroformylation reactions include, for example, mixed butenes, e.g., Raffinate I, II and III which generally comprise mixtures of $C_4$ such as 1-butene, cis/trans-2-butene, and isobutene, and alkanes such as butane and isobutane. Further such olefinic unsaturated compounds and the corresponding aldehyde products derived therefrom may also contain one or more groups or substituents which do not unduly adversely affect the hydroformylation process or the process of this invention such as described, for example, in U.S. Pat. Nos. 3,527,809, 4,769,498 and the like.

Illustrative alpha and internal olefins include, for example, ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexene, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene, and the like, as well as, 1,3-dienes, butadiene, alkyl alkenoates, e.g., methyl pentenoate, alkenyl alkanoates, alkenyl alkyl ethers, alkenols, e.g., pentenols, alkenals, e.g., pentenals, and the like, such as allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclo-octadiene, camphene, linalool, tetrahydrobenzaldehyde, cyanocyclohexene and the like.

The reaction conditions of the hydroformylation processes encompassed by this invention may include any suitable type hydroformylation conditions heretofore employed for producing optically active and/or non-optically active aldehydes. For instance, the total gas pressure of hydrogen, carbon monoxide and olefin starting compound of the hydroformylation process may range from 1 to 10,000 psia. In general, however, it is preferred that the process be operated at a total gas pressure of hydrogen, carbon monoxide and olefin starting compound of less than 2000 psia and more preferably less than 500 psia. The minimum total pressure is limited predominately by the amount of reactants necessary to obtain a desired rate of reaction. More specifically the carbon monoxide partial pressure of the hydroformylation process of this invention is preferable from 1 to 1000 psia, and more preferably from 3 to 800 psia, while the hydrogen partial pressure is preferably 5 to 500 psia and more preferably from 10 to 300 psia. In general $H_2$:CO molar ratio of gaseous hydrogen to carbon monoxide may range from 1:10 to 100:1 or higher, the more preferred hydrogen to carbon monoxide molar ratio being from 1:10 to 10:1. Further, the hydroformylation process may be conducted at a reaction temperature from $-25°$ C. to $200°$ C. In general hydroformylation reaction temperatures of 50° C. to 120° C. are preferred for all types of olefinic starting materials. Of course non-optically active aldehyde products are desired, achiral type olefin starting materials and organophosphorous ligands are employed, and when optically active aldehyde products are desired prochiral or chiral type olefin starting materials and organophosphorous ligands are employed. Of course, the hydroformylation reaction conditions employed will be governed by the type of aldehyde product desired.

The hydroformylation processes encompassed by this invention are also conducted in the presence of an organic solvent for the metal-organophosphorous ligand complex catalyst and free organophosphorous ligand. The solvent may also contain water. Depending on the particular catalyst and reactants employed, suitable organic solvents include, for example, alcohols, alkanes, alkenes, alkynes, ethers, aldehydes, higher boiling aldehyde condensation byproducts, ketones, esters, amides, tertiary amines, aromatics and the like. Any suitable solvent which does not unduly adversely interfere with the intended hydroformylation reaction can be employed and such solvents may include those disclosed heretofore commonly employed in known metal catalyzed hydroformylation reactions. Mixtures of one or more different solvents may be employed if desired. In general, with regard to the production of achiral (non-optically active) aldehydes, it is preferred to employ aldehyde compounds corresponding to the aldehyde products desired to be produced and/or higher boiling aldehyde liquid condensation byproducts as the main organic solvents as is common in the art. Such aldehyde condensation byproducts can also be preformed if desired and used accordingly. Illustrative preferred solvents employable in the production of aldehydes include ketones (e.g. acetone and methylethyl ketone), esters (e.g. ethyl acetate, di-2-ethylhexyl phthalate, 2,2,4-trimethyl-1,3-pentanediol monoisobutyrate), hydrocarbons (e.g. toluene), nitrohydrocarbons (e.g. nitrobenzene), and ethers (e.g. tetrahydrofuran (THF) and sulfolane). Suitable solvents are disclosed in U.S. Pat. No. 5,312,996. The amount of solvent employed is not critical and need only be that amount sufficient to solubilize the catalyst and free ligand of the hydroformylation reaction mixture to be treated. In general, the amount of solvent may range from 5 percent by weight up to 99 percent by weight or more based on the total weight of the hydroformylation reaction mixture starting material.

The hydroformylation process of this invention may be carried out in batch or continuous mode, but it is typically conducted in a continuous mode. In general, continuous hydroformylation processes are well known in the art and may involve: (a) hydroformylating the olefinic starting material(s) with carbon monoxide and hydrogen in a liquid homogeneous reaction mixture comprising a solvent, the metal-organophosphorous ligand complex catalyst, and free organophosphorous ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; (d) recovering the desired aldehyde hydroformylation product(s) in any manner desired, and (e) returning the catalyst to the reaction zone. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without intentionally recycling the unreacted olefinic starting material(s). Alternatively the process may intentionally recycle unreacted olefin back to the reaction zone. Such types of recycle procedure are well known in the art and may involve the liquid recycling of the metal-organophosphorous complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The most preferred hydroformylation process of this invention comprises a continuous liquid catalyst recycle process. Suitable liquid catalyst recycle procedures are disclosed, for example, in U.S. Pat. Nos. 4,668,651; 4,774,361; 5,102,505 and 5,110,990.

In an embodiment of this invention, the aldehyde product mixtures may be separated from the other components of the crude reaction mixtures in which the aldehyde mixtures are produced by any suitable method. Suitable separation methods include, for example, solvent extraction, crystallization, distillation, vaporization, wiped film evaporation, falling film evaporation, phase separation, filtration and the like. The aldehyde products may be removed from the crude reaction mixture as they are formed through the use of trapping agents as described WO 88/08835. One method for separating the aldehyde mixtures from the other components of the crude reaction mixtures is by membrane separation. Such membrane separation can be achieved as set out in U.S. Pat. No. 5,430,194. One preferred method is vaporization at reduced, normal or elevated pressure.

Hydrolytic decomposition and rhodium catalyst deactivation can be prevented or lessened by treating at least a portion of the reaction product fluid derived from the hydroformylation process and which also contains phosphorus acidic compounds formed during the hydroformylation process with an aqueous buffer solution in an extraction zone sufficient to neutralize and remove at least some amount of the phosphorus acidic compounds from the reaction product fluid.

Following contact with the aqueous buffer, the organic phase is returned to the reactor system. Although the two phases are immiscible, some gradual entrainment of aqueous buffer into the reactor may occur. Some buffer, ligand degradation products, and/or salts thereof may be dissolved in the organic phase. Upset conditions may also cause episodic, inadvertent carryover of aqueous buffer into the reaction process. The result is the formation of acid metal salts in the reaction system from the reaction of the buffers with acidic ligand degradation products. These acid metal salts are typically sodium or potassium salts (not rhodium) of the corresponding conjugate acid, e.g., sodium phosphate. These salts may become insoluble either due to a reduction in the water content in the matrix, lower polarity of the matrix due to increasing olefin or aldehyde product content, or changes in counter-ions (e.g., phosphate exchanging with phosphonate). The physical (e.g., crystal or amorphous) form may also change due to hydrate formation changing the character of suspended solids rendering them less mobile (larger size, gelatinous, etc.) and with greater tendency to foul lower temperature spots in the system such as coolers and pipes.

Trace amounts of the product aldehyde will form the corresponding acid due to gradual oxidation. Introduction of buffer or acid metal salts into the reactor may cause these trace acids to form additional acid metal salts, which may exacerbate solubility issues.

Similarly, in those systems where amines are added, these acid salts of amines or ammonium acid salts may also precipitate and cause fouling. These ammonium salts may become insoluble either due to a reduction in the water content in the matrix or changes in counter-ions (e.g., phosphate exchanging with phosphonate). Examples of amine additives include imidazoles, pyrazoles, indazoles, 1,2-diazines, 1,3,5-triazoles, benzimidazoles, and piperidines such as 2,2,6,6-tetramethylpiperidine. Other polar species may also contribute to fouling some of which may not be formally considered salts. Examples include aldehyde phosphonic acids, such as hydroxybutylphosphonic acid (HBPA), hydroxypentyiphosphonic acid (HPPA), phosphorous acid ($H_3PO_3$), and phosphoric acid ($H_3PO_4$), and salts thereof. Other examples include hydrolysable phosphorous ligand fragments such as pyrroles, amines, halides, esters, and alcohols such as phenols and bisphenols (e.g., from phosphite and phosphine ligands) and species derived from hydrolysis of aldehyde heavies to heavy acids (and their salts), and the like.

Aqueous buffers used in U.S. Pat. No. 5,741,944 are generally salts of weak acids or bases but are usually Group 1 or 2 metal (Na, K, Ca, etc.) salts of weak acids. In some cases where amines are used, they generate ionic salts (ammonium salts) when they neutralize the acidic impurities. While the acid metal and/or ammonium salts are soluble in water, they are sparingly soluble in the reactor organic matrix. Small changes in the water concentration or composition of the organic matrix may cause changes in the solubility of the salts. For example, as the olefin feed contains more saturated alkane or less-reactive internal olefins (e.g., 2-butene), the amount of hydrocarbons may increase and the polarity of the organic phase may decrease. Changing the catalyst flow through the extraction zone (during upsets, maintenance, etc.) could change the amount of water being dissolved in the catalyst layer which results in changes in water concentration in the organic matrix in the reactors. The build-up of non-polar aldehyde heavies may also change the organic matrix and its ability to keep salts in solution.

Generally speaking, the amount of water in the reaction zone is determined by several factors including but not limited to the water content of the feeds, product separation mode and conditions, and the solubility of water in the reaction fluid in the extraction zone. The direct addition of water to the HRF may allow higher concentrations of dissolved water in the HRF than described U.S. Pat. No. 5,744,649. While the '649 patent teaches adding buffer solution to the reaction zone which would also increase water, this also increases the concentration of salt in the reaction fluid which is counter-productive in dissolving and removing salts. Solubility is typically described as the Solubility Product which is the product of the [cation] times the [anion] in which the [cation] is the metal concentration and the [anion] is the concentration of the conjugate weak acid anion from the buffer or phosphorous degradation impurity (typically alkyl phosphonium acid or phosphorous acid). Since adding buffer increases the cation concentration, adding buffered water lowers the solubility of all dissolved metal salts including the foulant. This may also cause the buffer itself to precipitate making the fouling problem even worse.

When the water concentration in the reaction fluid is low (e.g., less than 0.1 wt % water), the acid metal salts are well behaved, i.e., they are suspended solids which are not expected to foul. Surprisingly as the water level increases, the acid metal salts become voluminous gels and sticky solids which can cling to cool surfaces and cause fouling of heat exchangers.

Surprisingly it has been found that moderately higher levels of non-buffered water will dissolve the deposited material and mitigate fouling. Moreover this addition of water does not appreciably accelerate ligand hydrolysis or negatively impact the overall system performance. The deposited material which is now dissolved is removed by the extractor thus the fouling problem is mitigated. Without being bounded by theory, it is hypothesized that since the foulants have already been neutralized, they do not act as strong acids and do not participate in the autocatalytic acid-catalyzed decomposition of the hydrolysable phosphorous ligands. Even though the water levels may be higher than that previously used, significant hydrolysable phosphorous ligand hydrolysis is not observed. This is in contrast to U.S. Pat. No. 5,741,944 where the solids are strong acids and it would be undesirable to dissolve them and increase their concentration in solution. While U.S. Pat. No. 5,744,649 adds water to the system, this is for acidity control which is not occurring in the present invention (acidity control has already occurred prior to the addition of water). U.S. Pat. No. 5,744,649 also teaches that the water must produce a separate layer which is not needed in the present invention.

The addition of the water may occur at any location within the reaction system outside of the aqueous extraction zone. This would include the reactors, heat exchangers, product separation zones (membrane separators, vaporizers, etc.), or feeds. Although water is added, the process is essentially "non-aqueous" in that the water present in the reaction medium is not present in an amount sufficient to cause either the particular reaction or said medium to be considered as encompassing a significant separate aqueous or water phase or layer in addition to the organic phase.

When using a countercurrent extractor such as in U.S. Pat. No. 5,741,944, adding another extraction zone downstream of the aqueous buffer extraction zone—which contains water only—is another example of the current invention. In that embodiment, the rising organic reaction fluid passes through a water layer and thus any dissolved or entrained salts are removed prior to the organic reaction fluid returning to the reaction zone. This water extraction zone may be a separate unit or a separate zone within a counter-current extractor (a dual-zone extractor) where in the bottom zone is primarily a buffer extraction zone (removing acids) and the upper zone is a salt scrubbing zone.

Water added in the present invention may contain buffer to maintain pH during storage, etc. but should be no more than 50, preferably no more than 20 and even more preferably than 10, percent of the concentration of the buffer used in the extraction step. For solubility reasons, it is preferred that the dilute buffer in the added water is not the same ion of the primary buffer (e.g., the buffer of the added water is a potassium carbonate salt and the buffer used in the extraction zone is a sodium phosphate salt). The amount of added water introduced into the HRF can vary but is typically 0.1, or 0.2, or 0.3 or 0.4 or 0.5 or more percent based on the weight of the HRF. The maximum amount of added water that can be introduced into the process is typically a function of practical considerations such as cost, diminishing returns, ease of operation, etc., but typically the maximum amount of added water contacted with the HRF does not exceed 5, or 4, or 3, or 2, or 1 percent based on the weight of the HRF.

FIG. 1 illustrates one embodiment of a hydroformylation process and the various locations at which the added water can be introduced into it. The process comprises a reaction zone 1 (typically contained or housed in one or more continuous stirred tank reactors or columns) in which olefin and synthesis gas are contacted under hydroformylation conditions to produce a hydroformylation reaction product in a hydroformylation reaction fluid. The HRF is transferred through conduit, e.g. pipe, 2 to separation zone 3 (also typically housed in a column) in which product, e.g., aldehydes, are recovered, certain byproducts vented, and unreacted starting materials and catalyst ("recycle HRF") are recycled back to reaction zone 1 via conduits 4, 4b and 7. Some of the recycle HRF in conduit 4 is withdrawn and passed through conduit 4a to buffer extraction zone 5 in which it is contacted with aqueous buffer solution. Buffer extraction zone 5 is typically housed in a column with the recycle HRF passing up through the column and the aqueous buffer solution passing down through the column in a countercurrent manner. Excess buffer passes out of buffer extraction zone 5 through the bottom of the column, and buffered recycle HRF out of buffer extraction zone 5 through the top of the column, through conduit 6, into conduit 7 and back to reaction zone 1. The part of the recycle HRF not passed through buffer extraction zone 5 passes unbuffered through conduit 4b, into conduit 7 in which it is mixed with buffered recycle HRF from buffer extraction zone 5, and back into reaction zone 1. The added water of this invention can be introduced into the process at any point outside of buffer extraction zone 5, i.e., at reaction zone 1, separation zone 3, and/or any of conduits 2, 4, 4a, 4b, 6 and/or 7.

Figure 2:
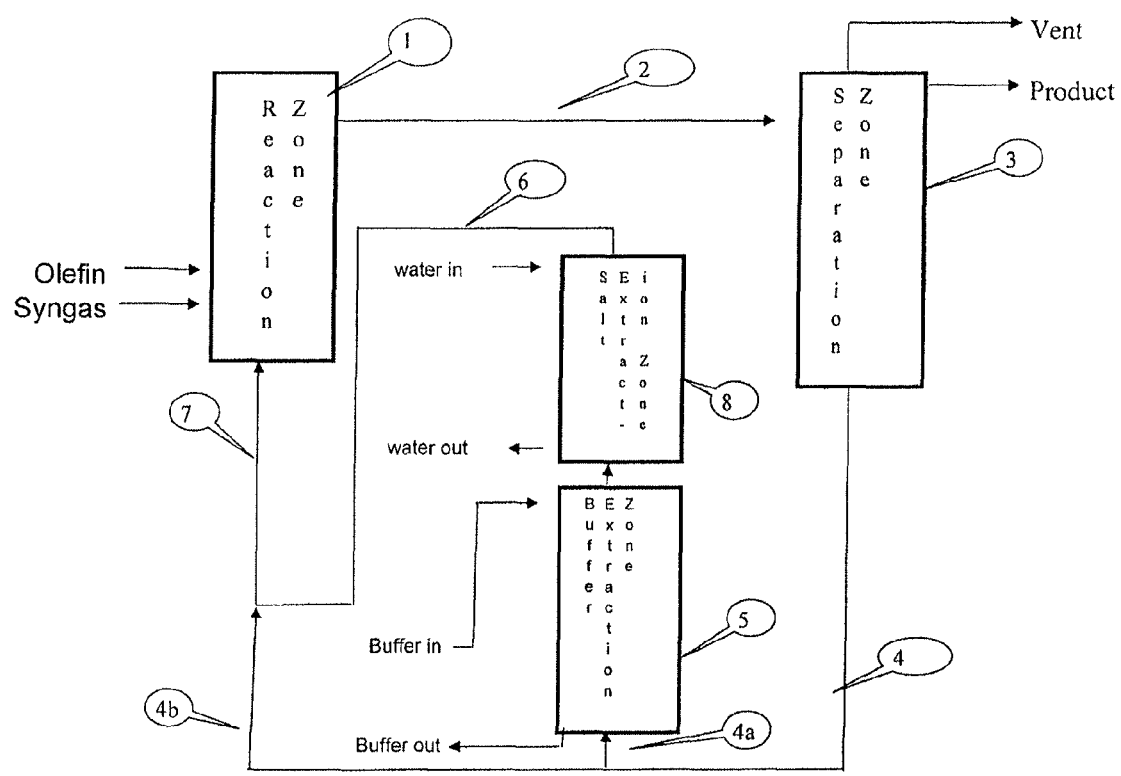
FIG. 2 is a schematic illustration of an embodiment of the process of FIG. 1 in which a salt extraction zone is housed in a vessel separate and apart from a vessel housing the buffer extraction zone, the salt extraction zone positioned downstream of the buffer extraction zone and upstream of the reaction zone.

FIG. 2 illustrates a variation on the embodiment of FIG. 1 in which salt extraction zone 8 is located above and downstream of extraction zone 5. In this variation, buffered recycle HRF passes out of the top of the column housing buffer extraction zone 5 into salt extraction zone 8 (in this embodiment housed in a column separate and apart from the column housing buffer extraction zone 5). The buffered recycle HRF passes up through the column housing salt extraction zone 8 making contact with the added water passing down through the column in countercurrent fashion. Excess water is removed from the bottom of the column housing salt separation zone 8. As shown in FIG. 2, added water can also be introduced into the process at the same points as shown in FIG. 1 although with the introduction of the added water to salt separation zone 8, any further addition of added water is typically unnecessary to obtain the benefits of this invention.

Figure 3:
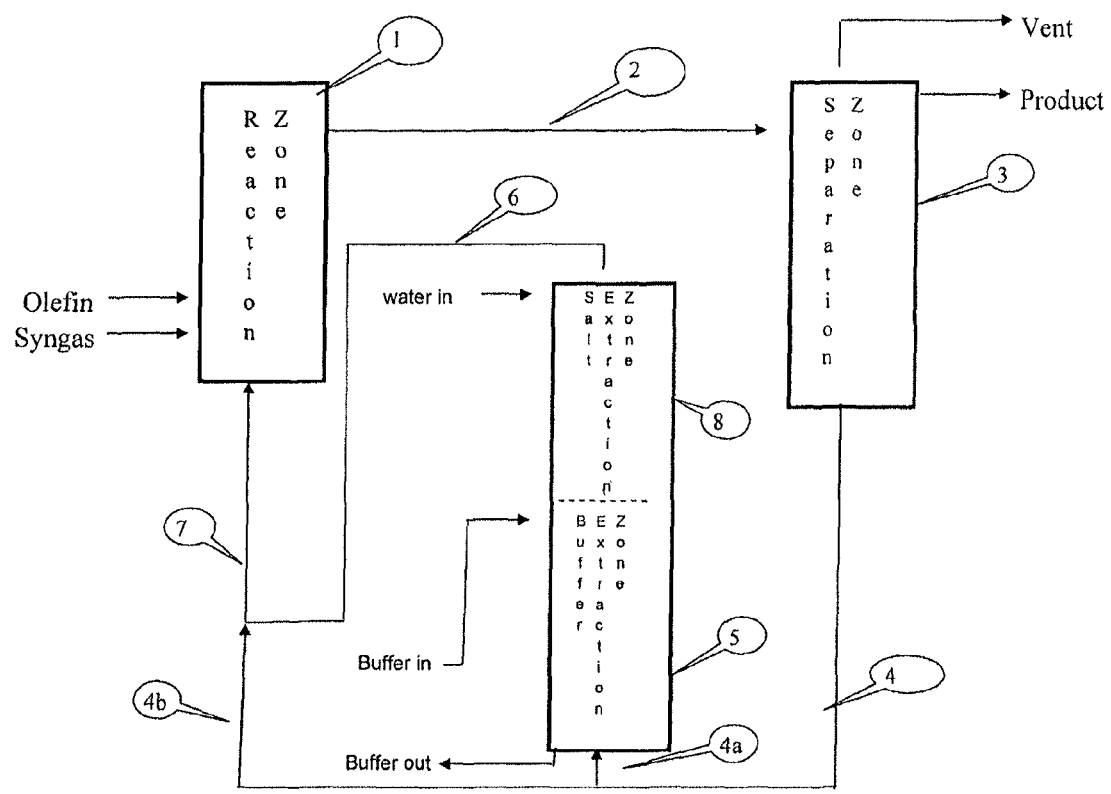
FIG. 3 is a schematic illustration of an embodiment of the process of FIG. 2 in which the salt extraction zone and buffer extraction zone are housed in a single vessel, and in which the salt extraction zone is downstream from the buffer extraction zone.

FIG. 3 illustrates a variation on the embodiment illustrated in FIG. 2, i.e., housing salt extraction zone 8 located within the same vessel (e.g., column) that houses buffer extraction zone 5. In this embodiment salt extraction zone is still located above and downstream of buffer extraction zone 5, i.e., the buffered recycle HRF passes out of buffer extraction zone 5 into salt extraction zone 8, and although the two zones can be physically separated by mechanical means, e.g., a baffle, typically they are not separated by any physical means. The principal difference between the two zones is that added water, either only lightly buffered or unbuffered is added to the salt separation zone while buffered water (not added water) is added to the buffer extraction zone. The added water is typically introduced into the top of the column while the buffered aqueous stream is added to the column at a point below which the added water is added, e.g., near or at the center of the column. Both excess added water and buffered aqueous solution are recovered from the bottom of the column.

The water level in the hydroformylation reaction fluid can readily be determined by conventional means such as Karl-Fischer or on-line spectroscopic methods such as infrared (IR) or near-infrared (NIR). Dissolved or entrained salt levels in the hydroformylation reaction fluid or extractor tails can be determined by ion chromatography, NMR ($^{31}P$ or $^{13}C$), atomic absorption (for Na, for example), or other conventional means. Fouling may be manifested by less-than-design heat transfer efficiency of heat exchangers, higher pressure drops through equipment (or restricted flow) and similar processing problems that typically get worse over time. In some instances, samples taken from of the reaction fluid may exhibit haziness, cloudiness, or solids upon cooling. Ligand concentration in the hydroformylation reaction fluid can be measured by conventional means such as $^{31}P$ NMR, GC, GPC, UV-Vis, or HPLC which allows the calculation of ligand decomposition rate over time. Likewise, the rate of heavies formation can be determined by GC analysis of hydroformylation reaction fluid samples taken over time.

The invention is further described by the following examples. Unless otherwise noted, all parts and percentages are by weight.

Specific Embodiments

Valeraldehyde was freshly distilled under reduced pressure prior to use. Valeraldehyde trimers were obtained by vacuum distillation of a commercial catalyst recycle sample. The distillate was determined to be a mixture of 75% valeraldehyde trimers and 25% valeraldehyde dimers by gas chromatography and mass spectrometry (GC/MS). A portion of both valeraldehyde and valeraldehyde trimers was saturated with water, and then blended with freshly distilled material to provide solutions of varying water levels. Unless otherwise noted, all water concentrations were determined by Karl-Fischer titration.

Comparative Example 1

One small portion (15 mg) of a disodium salt of hydroxypentylphosphonic acid (HPPA-$Na_2$) was charged to a 20 ml glass vial under nitrogen. Anhydrous valeraldehyde (3.52 g; 0.0961 wt % water) was added and the resulting mixture was stirred at room temperature. After stirring for two hours, the solids remained free-flowing, suspended particulates.

Examples 1-3

One small portion (70 mg) of a disodium salt of hydroxypentylphosphonic acid (HPPA-$Na_2$) was charged to each of three, 3 oz glass pressure vessels. Valeraldehyde, valeraldehyde trimers (2:1 weight ratio) and 1-butene were then added via syringe and stirred at room temperature for two hours. The observations are reported in Table 1:

TABLE 1

Examples 1-3 Observations

| Example | val/val trimer (g) | 1-butene (g) | Water (%) | Observations |
|---|---|---|---|---|
| 1 | 8.42 | 2.41 | 0.29 | Voluminous, gelatinous material |
| 2 | 8.94 | 2.26 | 0.87 | Mixture of gel and sticky solids |
| 3 | 8.97 | 2.22 | 1.47 | Sticky material on glass surface |

Examples 4-6

One small portion (130-160 mg) of the disodium salt of hydroxypentylphosphonic acid (HPPA-$Na_2$) was charged to each of three, 3 oz glass pressure vessels. Valeraldehyde, valeraldehyde trimers and 1-butene were then added via syringe and the resulting mixtures (which contained various levels of water) were stirred vigorously at 70° C. for two hours. Samples were then removed at temperature, quickly filtered, and the filtrate was twice extracted with water to facilitate the quantization of HPPA-Na$_2$ solubility by ion chromatography. The results are reported in Table 2.

TABLE 2

Examples 4-6 Observations

| Ex. | Val. (wt %) | Val Trimer (wt %) | 1-butene (wt %) | Water (wt %) | Description | HPPA-Na2 solubility (ppm) |
|---|---|---|---|---|---|---|
| 4 | 52.0 | 26.0 | 21.2 | 0.103 | Hazy watery solution | 4.8 |
| 5 | 52.1 | 26.0 | 21.1 | 0.380 | Very hazy liquid | 15.5 |
| 6 | 52.7 | 26.4 | 20.8 | 0.860 | Solid gel | 21.3 |

The solutions of Examples 4-6 were intended to model actual hydroformylation solution conditions. Examples 4-6 clearly show that modest increases in the water content have a dramatic impact on the solubility of HPPA-Na$_2$ to the extent that the HPPA-Na$_2$ concentration can be removed at or above the rate at which it is formed.

Example 7

A small portion (67 mg) of the disodium salt of hydroxypentylphosphonic acid (HPPA-Na$_2$) was charged to a 3 oz glass pressure vessel. A 2:1 mixture of valeraldehyde and valeraldehyde trimers (4.07 g) was added, and stirring was initiated at room temperature. Butene-1 (1.22 g) was added via syringe, and the tube was placed in an oil bath at 70° C. Additional water was slowly added to determine solubility properties under simulated hydroformylation reaction conditions. Total water content is based on the initial water level (determined by K—F titration) plus the incremental water additions made throughout. The results are reported in Table 3.

TABLE 3

Example 7 Observations

| Temperature (° C.) | Water content (%) | Additives | Result |
|---|---|---|---|
| 22 | 0.86 | None | Opaque with sticky, gelatinous solids on flask and turbid liquid. |
| 22 | 0.86 | 1.22 g 1-butene | No change |
| 70 | 0.86 | None | No change |
| 70 | 3.19 | 0.1 mL water | No change |
| 70 | 5.54 | 0.1 mL water | Less turbid |
| 70 | 7.72 | 0.1 mL water | Much less turbid; solids gone |
| 70 | 9.8 | 0.1 mL water | Clear solution |

The gelatinous material formed by disodium hydroxypentylphosphonic acid in the presence of low levels of water (<1%) at room temperature did not re-dissolve upon heating to reaction conditions thus salts formed or precipitated at extractor temperatures would be expected to persist in the reactors and stick to process equipment surfaces. Example 7 clearly shows that addition of water dissolves the precipitated solids under process conditions.

Combining the observations of Examples 1-3 and 4-6 with Example 7, one sees a trend where the physical appearance and nature of the mixture changes as a function of water content. At very low water content (e.g., 0.1 wt %) relative to the HRF, acid metal salt, HPPA-Na$_2$ is a suspended solid unlikely to cause fouling. As the water level increases, a voluminous, gelatinous material forms that could be capable of fouling surfaces. Further increases in water content converts the gel to a sticky solid which could readily deposit on and foul reactor surfaces. At even higher levels, the solids dissolve or become suspended in the organic matrix such that they would be transported to the extraction zone in a continuous recycle system where they would be removed.

As can be seen from the data, under some circumstances where the rate of ligand decomposition and/or acid and/or salt formation is higher than their removal rate, the concentration of these materials can be higher than their solubility in the hydroformylation reaction fluid, and fouling may result. In the case where the solubility is exceeded, the materials may cause fouling in the system and may not adequately be removed in the extraction zone. The present invention allows for either increasing the solubility of these salts by increasing the water content of the hydroformylation reaction fluid (without increasing the common ion concentration) or by removing (scrubbing) out common ions thus increasing the salt solubility. The solubilized foulants would be expected to be removed in the extraction zone.

Example 8

Raffinate 2 was hydroformylated continuously in a bubble column reactor equipped with a cooling loop in the presence of a rhodium catalyst complexed with an organobisphosphite ligand, free ligand, hydrogen, carbon monoxide and solvent (2,2,4-trimethyl-1,3-pentanediol monoisobutyrate) to give a mixture of n-valeraldehyde with 2-methylbutanal and 3-methylbutanal (isovaleraldehydes). The heat of reaction was removed by means of a water-cooled heat exchanger installed within the cooling loop. The hydroformylation reaction fluid discharged from the hydroformylation reactor was transferred to a separation zone for recovery of the valeraldehydes formed. The residual hydroformylation reaction fluid remaining after valeraldehyde separation was extracted with sodium phosphate buffer solution and then returned to the hydroformylation reactor as depicted in FIG. 1. Two days after start-up of the plant fouling at the heat exchanger was detected. The plant was operated for four more days. During these four days fouling increased to the point that the heat of reaction could no longer be sufficiently removed, thus causing an increase in temperature in the hydroformylation reactor and the hydroformylation reaction fluid. This loss of heat removal necessitated a plant shut down.

After thorough cleaning of the reactor, conduits, heat exchanger, control valves, pumps and other plant equipment which had been in contact with the hydroformylation reaction fluid the plant was started up again under the same process conditions as used before. After two days of operation fouling at the heat exchanger reoccurred.

Following the reoccurrence of fouling, equipment changes were made to allow the continuous addition of deionized water to the reactor until the water content in the hydroformylation reaction fluid (HRF) had increased by approximately 0.15%. One day after that addition of water a significant decrease of fouling at the heat exchanger and dissolution of the sticky, gelatinous precipitate on the heat exchanger plates could be noticed. Operation of the plant could be continued without necessitating shutdown as a result of insufficient heat transfer caused by fouling. The water content of the hydroformylation fluid was maintained at this level and fouling did not reoccur.

Although the invention has been described with certain detail through the preceding description of the preferred embodiments, this detail is for the primary purpose of illustration. Many variations and modifications can be made by one skilled in the art without departing from the spirit and scope of the invention as described in the following claims.

What is claimed is:

1. In an extraction process for removing metal salts from an organic hydroformylation reaction fluid ("HRF") prior to returning the HRF to a reaction zone of a hydroformylation process, the HRF comprising an organophosphorous ligand and a metal-organophosphorous ligand complex, the extraction process comprising the step of contacting the HRF with an aqueous buffer solution within a buffer extraction zone of the hydroformylation process, the reaction zone located upstream of the buffer extraction zone, the improvement comprising the step of contacting outside of the buffer extraction zone the HRF with water in addition ("added water") to the water present in the aqueous buffer solution.

2. The extraction process of claim 1 in which the hydroformylation process further comprises a product separation zone located downstream of the reaction zone and upstream of the extraction zone, and the added water and the HRF are contacted with one another in at least one of the reaction zone or the separation zone.

3. The extraction process of claim 1 in which the added water is contacted with the HRF downstream of the extraction zone and prior to the return of the HRF to the reaction zone.

4. The extraction process of claim 1 further comprising a salt extraction zone located downstream of the buffer extraction zone, and the HRF is contacted with the added water in the salt extraction zone and prior to the return of the HRF to the reaction zone.

5. The extraction process of claim 4 in which the salt extraction zone and buffer extraction zone are located in separate vessels.

6. The extraction process of claim 4 in which the salt extraction zone and the buffer extraction zone are located in a single vessel.

7. The extraction process of claim 4 in which the hydroformylation process further comprises heat exchangers and the added water is contacted with the HRF prior to the HRF entering the heat exchangers.

8. The extraction process of claim 1 in which the added water is not buffered.

9. The extraction process of claim 1 in which the added water is buffered.

10. The extraction process of claim 9 in which the buffer concentration of the added water is less than 50 percent of the concentration of the aqueous buffer solution.

11. The extraction process of claim 9 in which the buffer concentration of the added water is less than 20 percent of the concentration of the aqueous buffer solution.

12. The extraction process of claim 9 in which the buffer concentration of the added water is less than 10 percent of the concentration of the aqueous buffer solution.

13. The extraction process of claim 1 in which the amount of added water is 0.1 percent or more based on the weight of the HRF.

14. The extraction process of claim 1 in which the aqueous buffer solution comprises a metal salt of a weak acid.

* * * * *